United States Patent [19]

Ruprecht

[11] Patent Number: 5,512,281
[45] Date of Patent: Apr. 30, 1996

[54] MAMMALIAN MODEL SYSTEM AND METHODS OF TESTING IMMUNO-OR DRUG PROPHYLAXIS OF FETAL INFECTION BY HIV-1 OR OTHER LENTIVIRUSES

[75] Inventor: Ruth M. Ruprecht, Brookline, Mass.

[73] Assignee: Dana-Farber Cancer Institute, Inc., Boston, Mass.

[21] Appl. No.: 908,679

[22] Filed: Jul. 2, 1992

Related U.S. Application Data

[63] Continuation-in-part of Ser. No. 788,142, Nov. 5, 1991, abandoned.

[51] Int. Cl.$^6$ .......................... A61K 49/00; A01N 63/00
[52] U.S. Cl. ...................... 424/93.6; 424/9.2; 424/208.1; 800/2; 800/DIG. 5
[58] Field of Search ................................... 800/2, DIG. 4, 800/DIG. 5; 424/9, 89, 93.6, 9.2, 208.1

[56] References Cited

PUBLICATIONS

Oleske et al., "Immune Deficiency Med.Syndrome in Children," J. Am. Assoc. 249: 2345–2349 (1983).
Rubinstein et al., "Acquired Immunodeficiency With Reversed $T_4/T_8$ Ratios in Infants Born to Promiscuous and Drug–Addicted Mothers," J. Am. Med. Assoc. 249: 2350–2356 (1983).
Scott et al., "Acquired Immunodeficiency Syndrome in Infants," N.E. J. Med. 310: 76–81 (1984).
Piot et al., "AIDS: Ani International Perspective," Science 239: 573–579 (1988).
Curran et al., "Epidemiology of HIV Infection and AIDS in the United States," Science 239: 610–616 (1988).
Ryder et al., "Perinatal Transmission of the Human Immunodeficiency Virus Type 1 to Infants of Seropositive Women in Zaire," N.E. J. Med. 320: 1637–1642 (1989).
Centers for Disease Control Morbid. Mortal. Weekly Rep. 40: 357–358 (1991).
Sharpe et al., "Retroviruses and Mouse Embryos: A Rapid Model for Neurovirulence and Transplacental Therapy," Science 236: 1671–1674 (1987).
Sharpe et al., "Maternal transmission of retroviral disease: Transgenic mice as a rapid test system for evaluating perinatal and transplacental antiretroviral therapy," Proc. Natl. Acad. Sci. USA 85: 9792–9796 (1988).
Sharpe et al., "Maternal Transmission of Retroviral Disease and Strategies for Preventing Infection of the Neonate," J. Virol. 63: 1049–1053 (1989).
London et al., "Experimental Congenital Disease with Simian Cytomegalovirus in Rhesus Monkeys," Teratology 33: 323–331 (1986).
London et al., "Congenital Cerebral and Ocular Malformations Induced in Rhesus Monkeys by Venezuelan Equine Encephalitis Virus," Teratology 16: 285–296 (1977).
London et al., "Teratological Effects of Western Equine Encephalitis Virus on the Fetal Nervous System of *Macaca mulatta*, " Teratology 25: 71–79 (1982).
London et al., "Induction of Congenital Hydrocephalus with Mumps Virus in Rhesus Monkeys," J. Inf. Diseases 139: 324–328 (1979).
Chakrabarti et al., "Sequence of simian immunodeficiency virus from macaque and its relationship to other human and simian retroviruses," Nature 328: 543–547 (1987).
Letvin et al., "Induction of AIDS–like Disease in Macaque Monkeys with T–Cell Tropic Retrovirus STLV–III," Science 230: 71–73 (1985).
Daniel et al., "Prevalence of Antibodies to 3 Retroviruses in a Captive Colony of Macaque Monkeys," Int. J. Cancer 41: 601–608 (1988).
Eichbert et al., "In Utero Infection of an Infant Chimpanzee with HIV," N.E. J. Med. 319: 722–723 (1988).
Jehuda–Cohen et al., "Presence of SIV Antibodies in the Sera of Infants Born to SIV–Seronegative Monkeys," J. AIDS 4: 204–205 (1991).
Nowak, "A New Primate Model For HIV–1 Infection," J. NIH Res. 4: 42 (1992).
Palca, "A Surprise Animal Model for AIDS," Science 256: 1630–1632 (1992).
Palca, "AIDS Vaccines: Chimps Protected From Infected Cells," Science 256: 1632 (1992).
Agy et al., "Infection of Macaca nemestrina by Human Immunodeficiency Virus Type–1," Science 257:103–106 (1992).
World Health Organization Meeting Report—Geneva, Sep. 14–15, 1989, "Biological S." 18:225–234.

*Primary Examiner*—Jasemine C. Chambers
*Attorney, Agent, or Firm*—Weingarten, Schurgin, Gagnebin & Hayes

[57] ABSTRACT

A mammalian model system for the pathogenesis of lentiviral, especially HIV-1, infection during fetal gestation is disclosed. The model system is used in methods of testing various regimens for prophylaxis of fetal lentiviral infection. In the model system, fetal infection is established in a pregnant mammal (e.g., a rhesus monkey, *Macaca mulatta* or a pigtailed macaque, *Macaca nemestrina*) by ultrasound guided inoculation of an inoculum of a lentivirus, e.g., SIV, into the amniotic fluid. The testing methods include the analysis of the effectiveness of potential immunotherapeutic and transplacental drug therapy regimens. The model will also allow testing which viral isolates are pathogenic to the developing fetus.

16 Claims, No Drawings

MAMMALIAN MODEL SYSTEM AND METHODS OF TESTING IMMUNO-OR DRUG PROPHYLAXIS OF FETAL INFECTION BY HIV-1 OR OTHER LENTIVIRUSES

RELATED APPLICATIONS

This application is a continuation-in-part of application Ser. No. 07/788,152, filed Nov. 5, 1991 now abandoned.

FIELD OF THE INVENTION

This invention relates to the prevention and treatment of lentiviral, especially HIV-1, infection of fetuses and newborns.

BACKGROUND OF THE INVENTION

As early as 1983, human immunodeficiency virus type-1 (HIV-1) infection and the various disease states caused by the virus (e.g., AIDS and ARC) were recognized in pediatric patients (Oleske et al. (1983) *J. Am. Med. Assoc.* 249: 2345–2349; Rubinstein et al. (1983) *J. Am. Med. Assoc.* 249: 2350–2356). In Europe and North America, infants account for a small but increasing portion of the new cases of HIV-1 infection (Scott et al. (1984) *NE J. Med.* 310: 76–81; Piot et al. (1988) *Science* 239: 573–579; Curran et al. (1988) *Science* 239: 610–616). However, due to lack of proper education and training of parents and adequate preventative measures, these numbers will soon increase drastically. In Central and East Africa, nearly 10% of all parturient women are seropositive. With an overall transmission rate of 30%, approximately 3% of all infants born in this part of Africa are expected to be infected (Ryder et al. (1989) *NE J. Med.* 320: 1637–1642). A recent report from the Centers for Disease Control indicates that cases associated with heterosexual HIV-1 transmission have been increasing steadily in the United States since 1986 (Centers for Disease Control (1991) *Morbid. Mortal. Weekly Rep.* 40: 357–358). New cases have occurred more frequently among women than men, and the rate of perinatal HIV-1 transmission in children has continued to increase (Centers for Disease Control (1991) *Morbid. Mortal. Weekly Rep.* 40: 357–358). These statistics call for an immediate search for effective methods to prevent establishment of fetal or newborn HIV-1 infection.

To test different therapeutic and prophylactic strategies and vaccines, an animal model of the course of HIV-1, or other lentiviral, fetal infection is important. Murine models to study transplacental or perinatal antiretroviral therapy are known (Sharpe et al. (1987) *Science* 236: 1671–1674; Sharpe et al. (1988) *Proc. Natl. Acad. Sci. (USA)* 85: 9792–9796; Sharpe et al. (1989) *J. Virol.* 63: 1049–1053). While experiments in these models yielded promising results, the existing murine models involve Type C retroviruses which lack the regulatory genes present in lentiviruses and differ significantly in their pathobiology from HIV-1. In addition, mammalian models utilizing rhesus monkeys have been established to study the course of non-retroviral fetal infection by simian cytomegalovirus, Venezuelan and Western equine encephalitis virus, and mumps virus (London et al. (1986) *Teratology* 33: 323–331; London et al. (1977) *Teratology* 16: 285–296; London et al. (1982) *Teratology* 25: 71–79; London et al. (1979) *J. Inf. Diseases* 139: 324–328).

Infection of rhesus monkeys (Macaca mulatta) with simian immunodeficiency virus (SIV) closely mimics HIV-1 infection in humans. Both HIV-1 and SIV are lentiviruses with similar molecular architecture (Chakrabarti et al. (1987) *Nature* 328: 543–547), and both cause immunodeficiency resulting in opportunistic infections as well as central nervous system damage (Letvin et al. (1985) *Science* 230: 71–73). However, in utero transmission of SIV in rhesus monkeys has not been well established. In one documented case, three infants were born SIV-infected in a captive macaque colony (Daniel et al. (1988) *Int. J. Cancer* 41: 601–608). Two more cases have been reported involving other species of monkeys (Eichberg et al. (1988) *NE J. Med.* 319: 722–723; Jehuda-Cohen et al. (1991), *J. AIDS* 4: 204–205). In one, a pregnant chimpanzee, inoculated intravenously with 100 50% tissue culture infectious doses ($TCID_{50}$) of HIV-1, gave birth to an HIV-1-infected infant which did not develop any sign of disease (Eichberg et al. (1988) *NE J. Med.* 319: 722–723). Recently, in a separate study, three infants (ages 26, 19 and 9 months) born to sooty mangabey monkeys, naturally infected with a simian immunodeficiency (SIV/smm) virus, were shown to have high levels of SIV-reactive antibodies and virus could be isolated from their peripheral blood mononuclear cells by cocultivation (Jehuda-Cohen et al. (1991), *J. AIDS* 4: 204–205). It was believed that the transmission of virus may have not occurred through scratches and bites, since most infants remain seronegative after such incidences (Jehuda-Cohen et al. (1991), *J. AIDS* 4: 204–205). However, proof for maternal transmission is lacking, and these isolated cases have not been reproducible.

When groups of five pregnant rhesus monkeys were injected with SIV in the first, second, or third trimesters respectively, none of the infants born to these mothers was virus positive (Fultz, data presented at the Gallo laboratory meeting, August, 1990.)

Recent developments suggest that pigtailed macaque monkeys (*Macaca nemestrina*) can be infected with HIV-1 and may provide researchers with a better animal model to study HIV-1 infection (Palca, (1992) *Science* 256: 1630–1632; Agy et al. (1992) Science, in press; *Journal of NIH Research* (1992) 4: 42). In addition to being less expensive and more abundant, pigtailed macaques develop viremia and signs of illness, e.g., fever and lymphadenopathy, soon after being infected and will be important as a model in studying the early course of HIV-1 infection.

SUMMARY OF THE INVENTION

The invention generally features a mammalian model system for lentiviral pathogenesis during gestation that includes a pregnant mammal having a fetus infected intraamniotically with a lentivirus. The mammal is preferably a primate, especially a rhesus monkey or pigtailed macaque monkey, and the lentivirus is preferably SIV or HIV-1. As infection of mammals with lentiviruses, especially the infection of rhesus monkeys with SIV or pigtailed macaque monkeys with HIV-1, closely mimics HIV-1 infection in humans, the model system is useful for testing the effectiveness of various proposed strategies to prevent the establishment of fetal and newborn HIV-1 infection in humans.

The method of infecting the fetus includes providing a pregnant mammal free of lentiviral infection, and inoculating the amniotic fluid of the pregnant mammal with a lentivirus in an amount that is effective in causing infection of the fetus. Preferably, the inoculation is ultrasound guided.

The methods for testing prophylaxis of fetal lentiviral infection include establishing a potential immuno- or drug therapeutic regimen for the pregnant mammal, inoculating the amniotic fluid of the pregnant mammal with an amount of infective lentiviral agent that is generally effective in causing infection of the developing fetus, and determining the effectiveness of the therapeutic regimen in preventing the establishment of lentiviral infection. The potential therapeutic regimens include passive immunotherapy, e.g., injecting the pregnant female with neutralizing monoclonal or polyclonal antibodies; active immunotherapy, i.e., injection with antigen sufficient to provoke an immune response; or transplacental drug therapy which includes injection or oral therapy of a pregnant female, prior to infection of the fetus, with a known therapeutic agent. It is also possible to establish the lentiviral infection in the fetus before instituting a therapeutic regimen and subsequently to test the effectiveness of a therapeutic agent in reducing the extent of infection.

To study lentiviral pathogenesis during gestation and test different means of prophylaxis, an animal model is required which results in fetal or newborn infection with a reproducibly high rate, thus making the study as cost-effective as possible. The use of mammals, and especially of monkeys, in research is limited and costly, necessitating careful planning so as to use minimum numbers with maximum efficiency in projects involving these animals. In nature, SIV-infected rhesus monkeys transmit the infection to their offspring very seldom. However, in the model system of the invention, fetal or newborn infection is established with a reproducibly high rate making use of the model very cost-effective.

DESCRIPTION OF THE PREFERRED EMBODIMENTS OF THE INVENTION

An appropriate model system for use in carrying out the methods of the invention has been determined to be a pregnant mammal, most usefully a pregnant rhesus monkey or pigtailed macaque monkey, whose fetus has been infected with a lentivirus via ultrasound-guided intraamniotic injection. In the development of the model system, intraamniotic inoculation was directly compared to uterotomy, and was found to be the preferred vehicle for introducing an infective virus into the fetus.

Development of Model System

Pregnant rhesus monkeys (*Macaca mulatta*) were obtained from the Texas Primate Center (Alice, Tex.) and held in quarantine for six weeks for complete clinical evaluation at the test facility The animals were (TSI Mason Research Institute, Worcester, Mass.). The animals were free of retroviral infection and tuberculosis.

The pathogenic SIV isolate $SIV_{mac251}$ was used for all animal studies. Stock virus employed in the uterotomy procedure (described below) was propagated in human or rhesus monkey peripheral blood mononuclear cells (H-PBM or M-PBM) and titrated in MT-4 cells (Harada (1991) *Science* 243: 1731; Pauwels (1987) *J. Virol. Methods* 16: 171). For ultrasound (US)-guided SIV inoculation, a virus stock which had been grown in H-PBM and titrated in adult rhesus monkeys by intravenous inoculation was used (gift of Dr. N. Letvin, New England Regional Primate Research Center, Southborough, Mass.).

To determine the viability of the virus stock in rhesus monkey amniotic fluid, Hut78 cells were plated in 6-well tissue culture dishes ($1\times10^5$ cells/2 ml Roswell Park Memorial Institute (RPMI) medium supplemented with 10% fetal bovine serum, penicillin, streptomycin and L-glutamine/well) with 0, 50, 100, and 200 μl of an amniotic fluid obtained from a normal rhesus monkey during the third trimester of pregnancy. After incubation for 2 h at 37° C., 320 $TCID_{50}$ (50% tissue culture infectious dose) of virus stock were added to each well, and SIV reverse transcriptase (RT) activity present in culture supernatants was determined 7 days later (Dayton et al. (1986) Cell 44: 941–947).

A group of four pregnant rhesus monkeys underwent uterotomy during the third trimester of pregnancy; one animal was left untreated. Experimental animals were placed on halothane after pre-anaesthesia and intubation, prepped and draped sterilely. A midline abdominal incision was performed, and the fetus was exposed using a surgical technique for fetal exposure developed by Dr. Ben Jackson (New England Regional Primate Research Center). The placenta was palpated, and a 3–5 cm incision was made away from the placenta between two preplaced stay sutures. About half of the amniotic fluid was removed sterilely via a 20 ml syringe and saved for replacement prior to closure. The amniotic membrane was then sutured to myometrium, and a fetal upper extremity was located and exteriorized. A 24-gauge Angiocath® was inserted into the cephalic vein and utilized for infusion of the virus which had been drawn up into the plastic sheath of the catheter rather than through a needle to minimize risk of accidental exposure. Light pressure was applied to the infusion site until hemostasis occurred. The strength of the SIV inoculum was estimated based on in vivo studies performed in adult rhesus monkeys and by comparison of $TCID_{50}$ with animal infectious dose. In animal virus titration studies, when the monkeys were inoculated intramuscularly with $10^3$–$10^4$ $TCID_{50}$ of $SIV_{mac251}$, all became infected (Desrosiers et al. (1989) *Proc. Natl. Acad. Sci. USA* 86: 6353–6357). Therefore, to ensure establishment of infection, fetuses were inoculated with a rather high SIV inoculum (1–$3\times10^3$ $TCID_{50}$). The upper extremity of the fetus was then repositioned in the uterine cavity, the amniotic fluid was replaced, and the incision was closed with two layers of continuous inverting sutures. The abdominal wall was closed according to routine procedures. Butorphanol tartrate (0.05 mg/kg, every 12 h) was used post-operatively for analgesia. Following surgery, the animals were allowed to carry their pregnancies to term and to delivery vaginally.

For ultrasound-guided inoculation of amniotic fluid, each pregnant rhesus monkey was monitored by ultrasound for fetal development, using a portable, real time linear array ultrasound system with 5 MHz transducer (Technicar, Denver, Colo.). The animal was sedated with ketamine hydrochloride (10 mg/kg), a small area of hair was shaved from the lower abdomen, and transabdominal scans were performed by placing the probe on the shaved area and using a transmission gel (ECHO Ultrasound, Lewiston, Pa.). Fetal age was determined by measuring the biparietal diameter as previously described (Tarantal et al. (1988) *Am. J. Primatol.* 15: 309–323) using internal calipers and electronic calculation. Between days 133–140 of gestation, a few ml of clear amniotic fluid were withdrawn, and 200 animal infectious doses of $SIV_{mac251}$, grown in H-PBM and titrated in adult rhesus monkeys by intravenous inoculation, were inoculated directly into the remaining amniotic fluid, avoiding the placenta. (For these studies, the SIV preparation titrated in vivo has been kindly provided by Dr. Norman Letvin, New England Regional Primate Research Center.) Following amniotic fluid inoculation, weekly blood samples were obtained from the pregnant females for virological studies.

After all virus inoculations, pregnant females or mother/infant pairs were physically and clinically evaluated regularly and blood samples were taken weekly. After establishment of infection, monthly samples were drawn for all virological studies. After birth, newborns were carefully followed for viremia and development of disease. The mothers were allowed to nurse their infants. Moribund animals or infants delivered by C-section were sacrificed with an anaesthetic overdose.

Necropsies were performed on all sacrificed fetuses and one mother. Tissues from various organs were fresh frozen or fixed in 10% neutral buffered formalin and sections were stained with hematoxylin and eosin.

For virological studies, peripheral blood mononuclear cells, isolated by Ficoll-Hypaque sedimentation, were cultured in RPMI-1640 supplemented with 20% fetal bovine serum, penicillin, streptomycin and L-glutamine in the presence of 15 µg/ml concanavalin A (Con A). The next day, they were cocultivated with either CEMx174 cells (Salter et al. (1985) *Immunogenesis* 21: 235) or Con A-stimulated H-PBM, obtained from normal volunteers, in the presence of 10 u/ml of recombinant human interleukin-2 (rIL-2, Genzyme Corporation, Cambridge, Mass.) in the above medium. Culture supernatants were analyzed for the presence of SIV RT activity every 4 days for 2 weeks. Sera were examined for the presence of anti-SIV antibodies by Western blot analysis as described previously (Barin et al. (1987) *J. Virol. Methods* 17: 55–61; Ohta et al. (1988) *Int. J. Cancer* 41: 115–122). Serum p27 antigen levels were measured using a commercially available enzyme-linked immunoassay kit specific for $SIV_{mac251}$ (Coulter Corporation, Hialeah, Fla.).

Small portions of various organs from aborted fetuses and one euthanized mother were collected aseptically and stored frozen separately for polymerase chain reaction (PCR) analysis of DNA isolated from tissues and M-PBM. About 50 to 100 mg of tissue obtained from various organs were transferred to separate petri dishes containing 1 ml of phosphate-buffered saline (PBS), cut into small pieces using sterile scissors, and centrifuged at 2,000×g for 1 min in Eppendorf tubes. Next, DNA was isolated from the pelleted tissue fragments as described elsewhere (Maniatis et al. (1982) Molecular Cloning, A Laboratory Manual (Cold Spring Laboratory), p.280). The isolated DNA was quantified and stored at 4° C. until use For M-PBM, $10^6$ cells were pelleted, washed once with PBS, and genomic DNA was isolated as above.

PCR was performed using the Gene Amp™ DNA Amplification Reagent kit (Perkin-Elmer-Cetus) as described elsewhere (Saiki et al. (1988) *Science* 239: 487–491). Briefly, 1 µg of genomic DNA was subjected to two rounds of PCR whenever required, using nested primers derived from env and U3 regions of 3' LTR of $SIV_{mac251}$. For the first round of PCR, 1 µg of genomic DNA from corresponding samples was amplified, whereas for the second round 5 µl of first round amplified product were incorporated into PCR reaction mixture. Oligonucleotides for first round amplification were: sense strand (nucleotides 9,101 to 9,121), 5'-GATCTGCGACAGAAACTCTTG-3'(SEQ. ID NO: 1); antisense strand (nucleotides 9,465 to 9,445), 5'-GCACTGTAATAAATCCCTTCC-3'(SEQ. ID NO: 2) ; and second round primers were: sense strand (nucleotides 9,147 to 9,170) 5'-GACTCTTAGGAGAGGTGGAAGATG-3'(SEQ. ID NO: 3); antisense strand, (nucleotides 9,490 to 9,471) 5'--CATGTCTAAGATTCTATGTC--3'(SEQ. ID NO: 4) (Hirsch et al. (1987) *Cell* 49: 307–309). The expected product lengths for the first round and second round amplification are 364 bp and 343 bp, respectively. The temperature cycling schedule was: 94° C. for 45 sec, 55° C. for 1 min, 72° C. for 1 min. This program was repeated 35 times. The final extension was for 10 min at 72° C. C. The same program was used for both rounds of amplification.

When the fetuses were inoculated intravenously during uterotomy with a high virus inoculum and the SIV status of all mother/infant pairs determined (as is summarized in Table 1), all infants or fetal tissues which could be evaluated exhibited signs of infection. However, as out of four inoculated fetuses only one survived the procedure, it was concluded that the fatality rate was too high for uterotomy to be useful for the preparation of the animal model.

TABLE 1

Clinical and laboratory data on mother/infant pairs following intravenous fetal inoculation with $SIV_{mac251}$

| Animal Identification | Inoculum[1] [TCID$_{50}$] | Live offspring (birth, days p.i.) | Miscarriage (days p.i.) | SIV positive[2] (days p.i.) | p27 antigen (pg/ml) (days p.i.) | Outcome |
|---|---|---|---|---|---|---|
| 307B, pregnant ♀ | none | 90-5 | — | — | — | living |
| 90-5, ♂ | none | | | | | living |
| 048T, pregnant ♀ | M-PBM [1024] | 90-3 (20) | — | (17) | 860 (17) | living, ↓ CD4$^+$ T cells |
| 90-3, ♀ infant | M-PBM [1024] | (20) | — | (28) | ND (28) | living, ↓ CD$^4$ T cells |
| 80T28, pregnant ♀ | M-PBM [1024] | — | 90-1 (1) | (7) | NA | living, ↓ CD$^4$ T cells |
| 344, pregnant ♀ | M-PBM [1024] | — | 90-2 (2) breech | NA | NA | sacrificed (6), lymphoid depletion[3] |
| 383B, pregnant ♀ | H-PBM [3200] | — | 90-4 (4) | (8) | | living |
| 90-4, stillborn fetus | H-PBM [3200] | — | (8) | | | pneumonia, high SIV load in some organs | p.i., post inoculation; TCID$_{50}$, 50% tissue culture infectious dose; NA, not available; ND, not detectable.
[1]$SIV_{mac251}$ was grown in either human or rhesus monkey PBM (H-PMB or M-PBM).
[2]Infection was documented via cocultivation of M-PBM with CEMx174 or H-PBM.
[3]This mother suffered from sepsis and hemorrhage due to obstetrical complications (breech). She could not be evaluated further because of the short time interval between inoculation and sacrifice.

Mother 048T was culture-positive 3 days prior to delivery and also had a high serum p27 antigen level. This indicates that SIV infected the mother retrograde, 17 days after her fetus was infected intravenously with a high SIV inoculum. Her infant (90-3) was culture-positive when the first blood sample was collected 8 days after birth, but had non-detectable levels of p27 antigen. Western blot analysis performed on plasma samples from this mother/infant pair showed that anti-p27 antibodies were present already in the infant's first blood sample collected 8 days after birth. In contrast, a blood sample collected simultaneously from the mother lacked such antibodies, indicating that infection of the fetus preceded maternal infection. The mother seroconverted only on day 32 p.i. Mothers 80T28 and 383B were SIV culture-positive 7 and 8 days after inoculation, respectively, and 6 and 4 days after losing their fetuses.

In the method that was found to be preferable, ultrasound-guided amniotic fluid inoculation was performed on a total of four mother/infant pairs all of which then proceeded normally with the pregnancy. The results of fetal SIV infection via amniotic fluid are summarized in Table 2.

ered her infected infant (91-6) 3 days later. Since rhesus monkeys consume their placentas soon after delivery, which usually occurs at night, the next two mothers were delivered by Caesarian section to obtain placentas. Their fetuses, although viable at the time of C-section, were sacrificed to determine SIV organ distribution. Fetus 91-7, which was delivered by C-section 14 days p.i., was not infected, but his mother CH682 and placental macrophages were shown to be SIV positive by PCR, implying that the virus infected the placenta first. Fetus 91-9, being delivered 28 days p.i., was viremic. The long delay before the appearance of infection suggests that the inoculum size used is close to the minimal infections dose for this route of infection given the extent of dilution in the amniotic fluid.

In the follow-up of the three surviving infected mother/infant pairs, it was observed that mother 048T (uterotomy procedure) carried her fetus to term, but delivered an infant (90-3) with a low birth weight. This female infant gained weight poorly and had failure to thrive even though she was normal neurologically. At one month of age, she developed lymphadenopathy in the inguinal and axillary areas. At

TABLE 2

Clinical and laboratory data on mother/infant pairs following ultrasound-guided amniotic fluid inoculation with $SIV_{mac251}$

| Animal identification | Live offspring (birth, days p.i.) | SIV positive[1] (days p.i.) | p27 antigen pg/ml (days p.i.) | Outcome |
|---|---|---|---|---|
| RC51, pregnant ♀ | infant 91-1 (31) | (28) | 740 (28) | living, ↓ CD4+ T cells |
| 91-1, infant ♂ | (31) | (31) | ND (31) | living, low birth weight, lymphadenopathy, failure to thrive, ↓ CD4+ T cells |
| CH690, pregnant ♀ | infant 91-5 (19) | (16) | NA | living, ↓ CD4+ T cells |
| 91-6, infant ♀ | (19) | (19) | NA | living, ↓ CD4+ T cells |
| CH682, pregnant ♀ | fetus 91-7 (14) | (14) | | living, ↓ CD4+ T cells |
| 91-7, fetus ♂ | (14) C-section | — | | sacrificed[2] |
| 419T, pregnant ♀ | fetus 91-9 (25) | — | | living, ↓ CD4+ T cells |
| 91-9, fetus ♂ | (25) C-section | (25) | | sacrificed[2] | p.i., days post SIV inoculation; NA, not available; ND, non detectable.
[1]Infection was documented by both cocultivation and PCR.
[2]Viable infants were sacrificed to study the organ distribution of SIV.

Mothers RC51 and CH690 were allowed to deliver vaginally after the US-guided SIV inoculation. Mother RC51 became viremic 4 weeks after inoculation, when her blood p27 antigen level was very high. Three days later, she gave birth to a viremic infant (91-1) who had a non-detectable level of p27 antigen. Western blot analyses performed on plasma samples obtained from this mother/infant pair showed that the infant's plasma sample was reactive to p27 significantly earlier than the mother's. The second mother (CH690) became culture-positive 2 weeks after inoculation and delivabout 6 months of age, she underwent a growth spurt, and all lymphadenopathy disappeared. Her recovery and normal growth pattern have persisted since. Twice the mother developed transient lymphadenopathy as well as splenomegaly one and three months p.i. This mother demonstrated low CD4:CD8 ratios through the study (Table 3). At present, both mother and infant are living without signs of disease.

TABLE 3

T-cell subset analyses

| Mother/infant pairs | Ratio of CD4+ to CD8+ of mother/infant pairs (days post SIV inoculation) | | | |
|---|---|---|---|---|
| *307B/90-5 | NA/0.9 | NA/0.6 | NA/0.8 | 0.7/0.7 |
| 048T/90-3 | NA/1.3 (62) | 0.3/1.3 (94) | 0.6/1.4 (150) | 0.5/1.1 (226) |
| RC51/91-1 | 0.5/NA (6) | 0.18/0.14 (58) | 0.3/0.8 (212) | 0.5/0.7 (245) |
| CH690/91-6 | 0.3/0.8 (19) | 0.3/1.0 (47) | 0.4/0.4 (162) | |
| CH682/91-7 | 0.4/NA (99) | | | |
| 419T/91-9 | 0.4/NA (41) | | | |

*This mother/infant pair were not inoculated with SIV.

For the mother/infant pairs subjected to amniotic fluid inoculation, one infant was born with low birth weight (91-1), and developed transient lymphadenopathy at 3 months of age. While this infant had a low CD4:CD8 ratio at 2 months of age, his ratio increased subsequently. The second infant (91-6) born SIV infected and with a low weight, developed transient lymphadenopathy at one month of age.

While several other mothers (80T28, 344, 3838) showed transient lymphadenopathy, none had opportunistic infections, malignancies or signs of neurological dysfunction.

The three surviving mother/infant pairs were followed longitudinally for their SIV status. All three mothers became eventually virus negative as determined by cocultivation, whereas their infants' blood samples yielded positive cultures for every sample collected. Once the mothers' cultures were negative (starting from days 124, 127 or 47, respectively for mothers 048T, RC51 and CH690), they remained so for all follow-up tests (up to 10 separate samples). All three mothers remained PCR positive, however. Except for mother CH690 and her infant (91-6), SIV sequences could only be detected after two rounds of amplification using nested primers, indicating low copy numbers of SIV in PBM.

Fetuses from mothers 344 and 80T28 (Table 1) demonstrated no significant lesions in any of the tissues tested. However, in fetus 90-4, the airways were filled with neutrophils and the alveoli were lined with immature epithelium. Other tissues from this fetus had no significant lesions. Mother 344 (Table 1) demonstrated lymphoid hypoplasia in the splenic tissue and had depleted lymph nodes.

The stillborn offspring of mother 344, fetus 90-4, was dissected carefully, and the SIV load of individual organs was analyzed by semiquantitative PCR. First round PCR analysis revealed high levels of SIV in lymph nodes, spleen, lungs, and skin in contrast to PBM or other organs, indicating tissue sequestration of SIV in the fetus.

Use

The procedure of the present invention can also be used to infect pigtailed macaque (Macaca nemestrina) fetuses with the human immunodeficiency virus type 1 (HIV-1), the causative agent of human AIDS. The use of HIV-1 in pigtailed macaques allows the use of the human AIDS virus proper in a primate model system and permits the study of passive immunotherapy to the pregnant female using human monoclonal antibodies with neutralizing activity against HIV-1.

The model system of the invention can be employed in a systematic screening of different modes of vaccination or therapy in prenatal immunosuppressive lentiviral infection. The treatment methods can be examined for effectiveness both pre- and post-establishment of fetal infection. In addition, the system can also be useful in investigating the pathogenesis of the infection itself.

Because the model system involves the inoculation of the amniotic cavity of a naive, retrovirus-free pregnant female, the mother will have no anti-SIV or anti-HIV-1 immune responses that could confound the analysis of a potential immunotherapeutic regimen. For passive immunotherapy, monoclonal or polyclonal neutralizing antibodies can be administered to the mother during gestation. At regular intervals, the fetal circulation can be sampled under ultrasound guidance, and blood samples withdrawn. These samples then can be analyzed in vitro for the level of neutralizing antibody titer against the virus in established tissue culture assays. If sufficient levels of neutralizing antibodies are found in the fetal circulation, the fetus can be challenged with live virus or infected cells by ultrasound-guided amniotic fluid inoculation. As an alternative route, the fetus can also be challenged with ultrasound-guided intravenous inoculation. The model system can be used to determine if prophylactic immunotherapy administered to the pregnant female provides sufficient levels of neutralizing antibody to protect the fetus against subsequent challenge with the virus. Alternatively, active immunization of the pregnant female can be tested for ability to protect the developing fetus against subsequent SIV or anti-HIV-1 challenge.

For transplacental drug therapy, the pregnant female is treated during gestation with an antiviral drug known to be effective against the lentivirus. At various intervals, the fetal circulation is sampled for drug levels, using ultrasound-guided blood sampling as described above. When sufficient levels of the antiviral drug are detected in the fetal circulation, the fetus is challenged with SIV or HIV-1. The fetal circulation is sampled at regular intervals to determine whether drug prophylaxis with the specific agent administered to the pregnant female is effective in protecting the fetus. The newborn can subsequently be followed for signs of SIV or HIV-1 infection and disease. The proposed experimental model permits in addition the examination of the teratogenicity of such drug regimens.

The therapeutic regimens found to be effective using the methods of the invention can then be used in methods for treating a pregnant woman suspected of having, or known to have, an HIV-1 infection. As fetal infection in humans occurs during gestation or at birth, a therapeutic regimen designed to prevent the establishment of the infection in the fetus is appropriate, provided the pregnant woman is presented for treatment prior to about the third trimester. If the fetus itself is already infected at the time of prenatal examination, then one of the alternative regimens described can be used in an attempt to decrease the fetal virus burden.

Any therapeutic agents administered to the pregnant woman would be provided orally, parenterally, or topically by routine methods in pharmaceutically acceptable inert carrier substances. Optimal dosage and modes of administration can readily be determined by conventional protocols.

As the technology described permits inoculation of SIV or HIV-1 at well-defined time-points during gestation, analysis of the pathogenicity of SIV or HIV-1 as a function of time during intrauterine development is possible. Thus, one can examine the influence of a pathogenic, immunosuppressive lentivirus on the developing immune system. One can also address questions of teratogenicity of the virus itself, especially if virus exposure occurs early during gestation, at the time of organogenesis. Secondly, one can also address whether certain virus isolates are inherently more pathogenic to a developing fetus than others. For instance, it is possible to inoculate molecularly cloned SIV or HIV-1 preparations, i.e., virus preparations that are well-defined with regard to their genetics, into the amniotic fluid and study infectivity and pathogenesis. Thirdly, one can assess whether for a given virus isolate, the inoculum strength has an influence on the pathogenicity. Various doses of virus can be inoculated at a given time point into amniotic fluid, and the pathogenicity can be assessed.

Other embodiments are within the following claims. For example, any mammal for which an associated lentivirus has been determined is appropriate for use in the model system and methods of the invention. At the present time these include sheep, horses, goats, cats, and cows, in addition to monkeys. Other species of monkey suitable for infection with SIV include cynomolgus monkeys and pigtailed macaques, among others. In the model system, the infection of the fetus can also be established by any other method of inoculation under ultrasound guidance, including intravenous injection.

---

What is claimed is:

1. A method for infecting a simian fetus with SIV or HIV-1, comprising the steps of:

providing a pregnant monkey of a species susceptible to infection by SIV or HIV-1, said pregnant monkey being free of SIV or HIV-1 infection; and inoculating the amniotic fluid of said pregnant monkey with SIV or HIV-1, respectively, in an amount effective to cause infection of the fetus with said respective SIV or HIV-1.

2. The method of claim 1 wherein said monkey is a rhesus monkey.

3. The method of claim 1 wherein said monkey is a pigtailed macaque monkey.

4. The method of claim 1 wherein said amniotic fluid is inoculated under ultrasonic guidance.

5. A method for testing prophylaxis of fetal SIV or HIV-1 infection comprising the steps of:

providing a pregnant monkey of a species susceptible to infection by SIV or HIV-1, said pregnant monkey being free of SIV or HIV-1 infection;

establishing a potential immuno- or drug prophylactic regimen for prevention of SIV or HIV-1 infection of the fetus of said pregnant monkey;

after said establishing step, inoculating the amniotic fluid of said pregnant monkey with SIV or HIV-1, respectively, in an amount effective to cause infection of the fetus with said respective SIV or HIV-1 in the absence of said prophylactic regimen; and determining the effectiveness of said prophylactic regimen in preventing establishment of said respective SIV or HIV-1 infection in said fetus.

6. The method of claim 5 wherein said monkey is a rhesus monkey.

7. The method of claim 5 wherein said monkey is a pigtailed macaque monkey.

8. The method of claim 5 wherein said establishing step comprises injecting said pregnant monkey with antibodies capable of neutralizing SIV or HIV-1 infection; and sampling the fetal circulation for sufficient levels of said antibodies.

9. The method of claim 8 wherein in said determining step, the effectiveness of said antibodies in preventing establishment of said infection is determined by sampling said fetal circulation for the presence of said SIV or HIV-1.

10. The method of claim 5 wherein said establishing step comprises injecting said pregnant monkey with an antiviral agent; and sampling the fetal circulation for sufficient levels of said antiviral agent.

11. A method for testing prophylaxis of fetal SIV or HIV-1 infection comprising the steps of:

providing a pregnant monkey of a species susceptible to infection by SIV or HIV-1, said pregnant monkey being free of SIV or HIV-1 infection;

inoculating the amniotic fluid of said pregnant monkey with SIV or HIV-1, respectively, in an amount effective to cause infection of the fetus with said respective SIV or HIV-1 in the absence of an immuno- or drug prophylactic regimen;

administering to said pregnant monkey an amount of a post-exposure immuno- or drug prophylactic agent to be tested; and determining the effectiveness of said agent in reducing said respective SIV or HIV-1 infection of said fetus.

12. The method of claim 11, wherein in said determining step, the effectiveness of said agent is determined by sampling said fetal circulation for continued presence of said SIV or HIV-1.

13. A method for treating a pregnant human suspected of carrying an HIV-1 infection, for prevention of establishment of the HIV-1 infection in the fetus comprising the steps of:

providing a prophylactic agent tested according to the method of claim 6 or claim 7; and administering to the pregnant human an effective amount of said agent in a pharmaceutically acceptable carrier substance.

14. The method of claim 11 wherein said monkey is a rhesus monkey.

15. The method of claim 11 wherein said monkey is a pigtailed macaque monkey.

16. A method for treating a pregnant human suspected of carrying an HIV-1 infection, for prevention of establishment of the HIV-1 infection in the fetus comprising the steps of:

providing a prophylactic agent tested according to the method of claim 14 or claim 15; and administering to the pregnant human an effective amount of said agent in a pharmaceutically acceptable carrier substance.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GATCTGCGAC AGAAACTCTT G        21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

GCACTGTAAT AAATCCCTTC C        21

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GACTCTTAGG AGAGGTGGAA GATG        24

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

CATGTCTAAG ATTCTATGTC                                        20